US009872941B2

(12) United States Patent
Hoang

(10) Patent No.: US 9,872,941 B2
(45) Date of Patent: Jan. 23, 2018

(54) ANTIMICROBIAL COMPOSITIONS AND METHODS FOR LOCKING CATHETERS

(71) Applicant: Becton, Dickinson and Company, Franklin Lakes, NJ (US)

(72) Inventor: Minh Quang Hoang, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/486,893

(22) Filed: Apr. 13, 2017

(65) Prior Publication Data

US 2017/0216493 A1    Aug. 3, 2017

Related U.S. Application Data

(63) Continuation of application No. 15/086,860, filed on Mar. 31, 2016, now Pat. No. 9,649,411, which is a continuation of application No. 11/679,230, filed on Feb. 27, 2007, now abandoned.

(60) Provisional application No. 60/777,382, filed on Feb. 28, 2006.

(51) Int. Cl.
*A61L 29/16* (2006.01)
*A61L 29/08* (2006.01)
*A61K 31/155* (2006.01)
*A61K 31/198* (2006.01)

(52) U.S. Cl.
CPC ............ *A61L 29/16* (2013.01); *A61K 31/155* (2013.01); *A61K 31/198* (2013.01); *A61L 29/085* (2013.01); *A61L 2300/206* (2013.01); *A61L 2300/21* (2013.01); *A61L 2300/216* (2013.01); *A61L 2300/404* (2013.01); *A61L 2300/42* (2013.01)

(58) Field of Classification Search
None
See application file for complete search history.

(56) References Cited

U.S. PATENT DOCUMENTS

| 5,335,373 | A | | 8/1994 | Dangman et al. |
| 5,629,006 | A | * | 5/1997 | Hoang .................. A01N 31/02 422/1 |
| 5,763,412 | A | | 6/1998 | Khan et al. |
| 6,166,007 | A | | 12/2000 | Sodemann |
| 6,299,610 | B1 | | 10/2001 | Finch et al. |
| 6,350,251 | B1 | | 2/2002 | Prosl et al. |
| 6,482,197 | B2 | | 11/2002 | Finch et al. |
| 6,592,564 | B2 | | 7/2003 | Finch et al. |
| 6,617,294 | B2 | * | 9/2003 | Narula .................. A01N 31/02 510/138 |
| 6,679,870 | B1 | | 1/2004 | Finch et al. |
| 2002/0022660 | A1 | | 2/2002 | Jampani et al. |
| 2003/0144362 | A1 | | 7/2003 | Utterberg et al. |
| 2004/0142829 | A1 | | 7/2004 | Tsao et al. |
| 2005/0008610 | A1 | | 1/2005 | Schwarz et al. |
| 2006/0024372 | A1 | * | 2/2006 | Utterberg ............. A61K 9/0014 424/488 |
| 2006/0205621 | A1 | | 9/2006 | Borazjani et al. |
| 2007/0059332 | A1 | | 3/2007 | Graham et al. |

FOREIGN PATENT DOCUMENTS

| CN | 1224351 A | 7/1999 |
| CN | 1255865 A | 6/2000 |
| EP | 1283050 A2 | 2/2003 |
| JP | 2002539895 A | 11/2002 |
| JP | 2004516041 A | 6/2004 |
| JP | 2004518693 A | 6/2004 |
| JP | 2005515838 A | 6/2005 |
| JP | 2006506192 A | 2/2006 |
| JP | 2006510414 A | 3/2006 |
| JP | 2007233463 A | 3/2006 |
| JP | 2006521177 A | 9/2006 |
| KR | 1020070088636 A | 8/2007 |
| WO | 9847501 A1 | 10/1998 |
| WO | 0057933 A1 | 10/2000 |
| WO | 0205188 A1 | 1/2002 |
| WO | 2006055397 A2 | 5/2006 |

OTHER PUBLICATIONS

Raad et al., "Intravascular Catheter-Related Infections: New Horizons and Recent Advances", Arch Intern Med.,vol. 162, Apr. 22, 2002, pp. 871-878.

* cited by examiner

*Primary Examiner* — Nannette Holloman
(74) *Attorney, Agent, or Firm* — The Webb Law Firm

(57) ABSTRACT

Antimicrobial compositions for use in locking catheters and other devices are provided. In some embodiments, the composition includes at least one alcohol, at least one biocidal agent which is not an alcohol, and one or more poloxamers; in other embodiments, the composition comprises at least one poloxamer and at least one alcohol. The composition can provide long-lasting antimicrobial activity. Methods of using the composition are also provided.

23 Claims, No Drawings

ANTIMICROBIAL COMPOSITIONS AND METHODS FOR LOCKING CATHETERS

CROSS REFERENCE TO RELATED APPLICATIONS

The present application is a continuation of U.S. patent application Ser. No. 15/086,860 filed on Mar. 31, 2016, entitled "Antimicrobial Compositions and Methods for Locking Catheters", now U.S. Pat. No. 9,649,411, which is a continuation of U.S. patent application Ser. No. 11/679,230 filed on Feb. 27, 2007, entitled "Antimicrobial Compositions and Methods for Locking Catheters", now abandoned, which claims priority to U.S. Provisional Application No. 60/777,382 filed on Feb. 28, 2006, entitled "Antimicrobial Compositions and Methods for Locking Catheters", the entire disclosures of each of which are hereby incorporated by reference.

FIELD OF THE INVENTION

The present invention relates generally to antimicrobial compositions, which compositions may be useful for catheter locking solutions or catheter coatings to reduce or prevent infection.

BACKGROUND OF THE INVENTION

Catheters, particularly intravenous (IV) catheters, are used for infusing fluid (such as saline solution, various medicaments and parenteral nutrition) into a patient, withdrawing blood from a patient and monitoring various parameters of the patient's vascular system. Generally, catheters include a lumen or reservoir which contains fluid or medication to be injected or dispensed into a patient's body and an injection port or device for access with a needle.

Complications associated with catheters include those related to their insertion, such as pneumo/hemothorax, arterial puncture, and nerve injury, and secondary problems occurring as a consequence of their use, such as thrombosis and infection. If a catheter becomes infected the patient will require additional treatment and perhaps removal of the catheter. In the case of transcutaneous catheters, skin penetration is a common route of infection. Catheter sepsis remains one of the major causes of morbidity and mortality in a patient receiving home parenteral nutrition. Implanted catheters can often become plugged or fouled over time. This is a problem with intravascular catheters, where clotting and thrombus formation within the catheter lumen can be problematic.

The majority of serious catheter-related infections are associated with central venous catheters (CVCs), especially those that are placed in patients in intensive care units (ICUs). In the ICU setting, the incidence of infection is often higher than in the less acute in-patient or ambulatory setting. Certain catheters (e.g., pulmonary artery catheters and peripheral arterial catheters) may be accessed multiple times per day for hemodynamic measurements or to obtain samples for laboratory analysis, augmenting the potential for contamination and subsequent clinical infection. A total of 250,000 cases of CVC-associated bloodstream infections (BSIs) have been estimated to occur annually, and the cost of CVC-associated BSI is substantial in terms of morbidity and in terms of financial resources expended.

To reduce problems associated with clotting and thrombus formation, it is now common to "lock" intravascular access catheters between successive uses. Locking typically involves first flushing the catheter with saline to remove blood and other substances from the catheter lumen. After the catheter has been flushed, an anti-coagulant solution, typically heparin, is then injected to displace the saline and fill the lumen. The heparin-locking solution prevents blood from entering the lumen and actively inhibits clotting and thrombus formation within the lumen. While some thrombus may still form at the distal tip of the catheter, the formation is usually minimal and presents few problems. It has further been proposed to combine various antimicrobial substances with the locking solution in order to inhibit infection at the same time that thrombus formation is being inhibited.

While generally effective, the use of heparin for catheter locking solutions suffers from a number of disadvantages. The need to prepare a heparin solution at the end of every catheter treatment session is time-consuming and presents an opportunity for caregiver error. Hemodialysis and hemofiltration patients may undergo such heparin locks at least several times a week, while patients on IV may have to undergo such heparin locks several times a day. The inconvenience and expense of performing heparin locks can be burdensome over time. Moreover, the need to combine a separate anti-microbial agent in the heparin lock solution further complicates the procedure and adds expense, and the addition of an anti-microbial agent to the heparin lock will generally be effective only within the lumen and at the openings from the lumen. There will be little reduction in the risk of infection in the regions surrounding the implanted catheter, including at the point of penetration through the skin where the risk of infection is the greatest. Some locking solutions have been designed to overcome this problem and to penetrate the material of the catheter to provide antimicrobial action in tissues surrounding the catheter.

U.S. Pat. No. 6,592,564 describes the use of lower alcohols for disinfecting implanted catheters. The alcohol diffuses through the porous material of the catheter or other implanted device, thereby providing antimicrobial activity to the surrounding tissue in addition to the interior of the device.

Alcohols are well-known for their disinfection properties. Rubbing alcohol containing 70% ethyl alcohol and 30% water, and isopropyl rubbing alcohol containing 70% isopropyl alcohol and 30% water are listed in the United States Pharmacopia (USP) official monograph XXIV, pages 60 and 927, respectively, as disinfectants. Recently published studies indicate that alcohol is a potent antimicrobial agent, and if used with surgical scrub, will cause significant mean log reduction of bacterial counts.

U.S. Pat. No. 6,350,251 discloses internal prosthetic devices such as catheters or ports including a biocidal lock comprising an anticoagulant and a non-antibiotic biocide.

In prior art compositions which are alcohol based, the alcohol evaporates very quickly or becomes diluted, and does not provide long-lasting antimicrobial activity. This results in the need for repeated flushing of the catheter and renewal of the antimicrobial composition when the time between uses of the catheter is long. There remains a need for an antimicrobial locking solution which can provide long-lasting action, without the need for additional applications in between uses of the catheter.

SUMMARY OF THE INVENTION

In some embodiments, the present invention provides antimicrobial compositions or catheter coatings comprising at least one poloxamer, at least 10% by weight of at least one alcohol on a basis of total weight of the antimicrobial composition, and at least one biocidal agent which is not an alcohol. In other embodiments, the present invention provides antimicrobial compositions or catheter coatings comprising at least one poloxamer and at least 10% by weight of at least one alcohol on a basis of total weight of the antimicrobial composition.

In some embodiments, the present invention provides methods for coating at least a portion of an interior surface of a catheter using the above antimicrobial compositions.

In some embodiments, the present invention provides methods for providing disinfection of a catheter comprising introducing an antimicrobial composition into a lumen of the catheter or coating at least a portion of the interior of the catheter with an antimicrobial composition, the antimicrobial solution comprising at least one alcohol, at least one biocidal agent that is not an alcohol, and at least one poloxamer. In other embodiments, the present invention provides methods for providing disinfection of a catheter comprising introducing an antimicrobial composition into a lumen of the catheter or coating at least a portion of the interior of the catheter with an antimicrobial composition, the antimicrobial composition comprising at least one alcohol and at least one poloxamer.

These and other aspects of the invention will become more readily apparent from the following detailed description and appended claims.

DETAILED DESCRIPTION OF THE INVENTION

A catheter is a tube that a health professional may insert into part of the body. In most uses it is a thin, flexible tube: a "soft" catheter; in some, it is a larger, solid tube: a "hard" catheter. Placement of a catheter into a particular part of the body may allow, for example, draining urine from the urinary bladder as in urinary catheterization; drainage of fluid collections, e.g. an abdominal abscess; administration of intravenous fluids, medication or parenteral nutrition; angioplasty, angiography, balloon septostomy; and direct measurement of blood pressure in an artery or vein. Also, implanted catheters enjoy widespread use in a number of medical procedures. Hemodialysis and hemofiltration both rely on separate draw and return catheters implanted into a vein to allow extracorporeal treatment of the blood. Peritoneal dialysis, in contrast, relies on a single catheter implanted in the peritoneum to permit introduction and withdrawal of dialysate to permit in situ dialysis.

There are many types of catheters used for intravenous administration of fluids and medication, including peripheral venous catheters (PVC); peripheral arterial catheters; midline catheters; nontunneled central venous catheters (CVC); pulmonary artery catheters; percutaneously inserted central catheters (PICC); tunneled catheters; totally implantable catheters; and umbilical catheters.

The most common site for insertion of an IV catheter is the veins in the arm (peripheral veins, hence the term "Peripheral Venous Catheter" (PVC)). A peripheral vein is any vein that is not in the chest or abdomen. Arm and hand veins are typically used, although leg and foot veins are occasionally used. Pediatricians sometimes use the scalp veins of infants. This type of IV therapy usually stays in place for two to three days, before either being removed or moved to a different site. The peripheral IV line consists of a short catheter (a few centimeters long) inserted through the skin into a peripheral vein. Part of the catheter remains outside the skin, with a hub that can be connected to a syringe or an intravenous infusion line, or capped with a bung between treatments. The caliber of cannulas is commonly indicated in gauge, with 14 being a very large cannula (used in resuscitation settings) and 24-26 the smallest. Blood can be drawn from a peripheral IV if necessary, but only if it is in a relatively large vein and only if the IV is newly inserted. A peripheral IV cannot be left in the vein indefinitely, because of the risk of insertion-site infection leading to cellulitis and bacteremia. Hospital policies usually dictate that every peripheral IV be replaced (at a different location) every three days to avoid this complication.

In situations where the patient requires longer treatment with an IV, a catheter will be inserted into a larger vein, usually one near the shoulder (subclavian vein) or neck (jugular vein). These types of catheters, referred to as "Central Venous Catheters" (CVC) extend into the tip of the heart (superior vena cava) to allow more direct and faster access to the bloodstream in the administration of medication and fluids and can remain in place for up to seven days. Central venous catheters that are required to remain in place for several weeks can be implanted (tunneled) under the skin and positioned in a large vein, with the ideal catheter exiting the skin on the patient's chest. A central IV line has several advantages over a peripheral IV. It can deliver fluids and medications that would be overly irritating to peripheral veins because of their concentration or chemical composition, such as some chemotherapy drugs and total parenteral nutrition. Medications reach the heart immediately, and are quickly distributed to the rest of the body. There is room for multiple parallel compartments (lumens) within the catheter, so that multiple medications can be delivered at once even if they would not be chemically compatible within a single tube. Caregivers can measure central venous pressure and other physiological variables through the line. However, central IV lines also carry higher risks of bleeding, bacteremia and gas embolism.

Longer-term central vein catheters can also be inserted into the large vein in the front of the elbow, the cubital fossa, which then extends up into the superior vena cava. This type of catheter is referred to as a peripherally inserted central catheter, or PICC, and can stay in the same vein for several weeks. PICCs are the most common form of IV therapy for home care patients. PICC catheters are commonly used in the hospital setting (acute care) such as intensive care units and critical care, but are also widely used in the home nursing environment and are usually indicated for patients who will require long-term therapy (several weeks to months).

The most common type of IV catheter is an over-the-needle peripheral IV catheter. As its name implies, an over-the-needle IV catheter is mounted over an introducer needle having a sharp distal tip. At least the distal portion of the catheter tightly engages the outer surface of the needle to prevent peelback of the catheter and thus facilitates insertion of the catheter into the blood vessel. The distal tip of the introducer needle extends beyond the distal tip of the catheter with the bevel of the needle facing up away from the patient's skin.

The catheter and introducer needle assembly is inserted at a shallow angle through the patient's skin into a blood vessel. There are many techniques for inserting such a catheter and introducer needle assembly into a patient. In one insertion technique, the introducer needle and catheter are inserted completely into the blood vessel together. In another technique, the introducer needle is partially withdrawn into the catheter after the initial insertion into the blood vessel. The catheter is then threaded over the needle and inserted completely into the blood vessel.

A PICC may have two parallel compartments, each with its own external connector (double-lumen), or a single tube and connector (single-lumen). From the outside, a single-lumen PICC resembles a peripheral IV, except that the tubing is slightly wider.

A port (often referred to by brand names such as Port-a-Cath or MediPort) is a central venous line that does not have an external connector; instead, it has a small reservoir implanted under the skin. Medication is administered intermittently by placing a small needle through the skin into the reservoir. Ports cause less inconvenience and have a lower risk of infection than PICCs, and are therefore commonly used for patients on long-term intermittent treatment.

In some embodiments, antimicrobial compositions of the present invention can be used as catheter locking solutions in any of the above catheter types, to provide antimicrobial protection to a patient having the catheter inserted or implanted into a portion of a patient's body, such as a vein. The locking solution can be placed into the catheter to provide short or long-term protection, for example from one hour up to about a week, typically on the order of from about 48 hours to about a week. This is achieved by a composition comprising at least one alcohol, at least one biocidal agent which is not an alcohol, and at least one poloxamer surfactant. In an alternative embodiment, the composition can comprise at least one poloxamer surfactant and at least one alcohol.

In some embodiments, at least a portion of the interior surfaces of the catheter (and any exterior surfaces as desired) can be coated with antimicrobial compositions of the present invention. Non-limiting examples of interior surfaces of the catheter that can be coated with antimicrobial compositions of the present invention include the lumen, tubing, plungers, caps, etc. The coating can be applied by any conventional method well known to those skilled in the art, such as dipping, spraying, etc. The coating can be applied as a solution as discussed below, and may optionally be at least partially dried. The thickness of the coating generally can range from about 1 µm to about 1 mm, as desired.

In some embodiments, the catheter having the interior coating can have a locking solution placed within the catheter. The locking solution can be any conventional locking solution or can be a locking solution of the present invention as discussed herein.

The antimicrobial composition of the present invention comprises one or more alcohols. Suitable alcohols include, for example, ethanol, isopropanol, propylene glycol, benzyl alcohol, chlorobutanol, phenylethyl alcohol and the like. In some embodiments, the at least one alcohol is a $C_1$-$C_6$ lower alcohol, such as ethanol or isopropanol. In other embodiments, the $C_1$-$C_6$ lower alcohol is a mixture of isopropyl alcohol and ethanol, in a ratio of about 1:10 to 1:1. While not intending to be bound by any theory, it is believed that the alcohol(s) can open the pore structure of the catheter material to facilitate penetration of the antimicrobial composition and may prolong the release rate of the antimicrobial composition. The one or more alcohols are present in an amount of at least 10 wt. %, preferably in the range of 50 to 95 wt. %, based on the total weight of the antimicrobial composition.

The antimicrobial composition of the present invention can further comprise at least one or more biocidal agents that are not an alcohol (as described above). The terms "biocidal agent" or "biocide," as used herein, mean an agent that destroys, inhibits and prevents the propagation, growth and multiplication of unwanted organisms. The term "organisms" includes, but is not limited to, microorganisms, bacteria, undulating bacteria, spirochetes, spores, spore-forming organisms, gram-negative organisms, gram-positive organisms, yeasts, fungi, molds, viruses, aerobic organisms, anaerobic organisms and mycobacteria. Specific examples of such organisms include the fungi *Aspergillus niger, Aspergillus flavus, Rhizopus nigricans, Cladosporium herbarium, Epidermophyton floccosum, Trichophyton mentagrophytes, Histoplasma capsulatum*, and the like; bacteria such as *Pseudomonas aeruginosa, Escherichia coli, Proteus vulgaris, Staphylococcus aureus, Staphylococcus epidermis, Streptococcus faecalis, Klebsiella, Enterobacter aerogenes, Proteus mirabilis*, other gram-negative bacteria and other gram-positive bacteria, mycobactin and the like; and yeast such as *Saccharomyces cerevisiae, Candida albicans*, and the like. Additionally, spores of microorganisms, viruses and the like are organisms within the scope of the present invention.

Biocidal agents suitable for use in the present invention include, but are not limited to, biocides such as phenol, quaternary ammonium biocides, chlorine-releasing biocides, quinoline, quinaldinium, thiosemicarbazone, quinone, sulfa, carbamates, salicylamide, carbanilide, amide, guanide, amidine, chelate and imidazoline biocides.

Other suitable biocides that can be used in the present invention include, for example, acetic acid, benzoic acid, sorbic acid, propionic acid, dehydroacetic acid, sulfurous acid, vanillic acid, esters of p-hydroxybenzoic acid, 2-bromo-2-nitropropan-1,3-diol, formaldehyde, glutaraldehyde, calcium hypochlorite, potassium hypochlorite, iodine (in various solvents), povidone-iodine, hexamethylenetetramine, noxythiolin, 1-(3-choroallyl)-3,5,7-triazo 1-azoniaadamantane chloride, taurolidine, taurultam, EDTA, N(5-nitro-2-furfurylidene)-1-amino-hydantoin, 5-nitro-2-furaldehyde semicarbazone, 3,4,4'-trichlorocarbanilide, 3,4', 5-tribromosalicylanilide, salicylanilide, 3-trifluoromethyl-4, 4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, sodium oxychlorosene, parachlorometaxylenol, 2,4,4'-trichloro-2'-hydroxydiphenol, silver sulfadiazine and silver nitrate.

Additional suitable biocides include dyes such as acridine, acriflavine, aminacrine hydrochloride, proflavin hemisulfate, triphenylmethane, magenta, crystal violet, scarlet red, pararosaniline, and rosaniline; chlorine releasing biocides such as sodium hypochlorite, oxychlorosene, chloramine, dichlorodimethylhydantoin, halazone, dichloramine, chlorasine, succinchlorimide, trichloroisocyanuric acid, dichloroisocyanurate, trichloromelamine, dichloroglycoluril, halogenated dialkyl-hydantoin, and halane; quinaldinium and quinoline biocides such as dequalinium, laurolinium, hydroxyquinoline, lioquinol, chlorquinaldol, halquinol, aminoquinuride, benzoxiquine, broxyquinoline, chloroxine, cloxyquin, ethylhydrocupreine, euprocin, hydrastine, 8-hydroxyquinoline, 8-hydroxyquinoline sulfate and iodochlorhydroxyquin; quaternary ammonium biocides including pyridinium biocides, benzalkonium chloride, cetrimide, benzethonium chloride, cetylpyridinium chloride, chlorphenoctium amsonate, dequalinium acetate, dequalinium chloride, domiphen bromide, laurolinium acetate, methylbenzethonium chloride, myristyl-gamma-picolinium chloride, ortaphonium chloride, and triclobisonium chloride; furans such as griseofulvin, nitrofurfural, nitrofurazone, nitrofurantoin, furazolidone, furaltadone, 2-(methoxymethyl)-5-nitrofuran, nidroxyzone, nifuroxime and nifurzide; phenol biocides such as chlorinated phenol, cresol, thymol, carvacol, acetomeroctol, fenticlor, chlorocresol, chloroxylenol, hexachlorophene, bisphenols, amylmetacresol, bithionol, chlorothymol, dichloroxylenol, chlorophene, p-chlorophenol, p-phenylphenol, trinitrophenol, dichlorobisphenol, bromochlorobisphenol, 1-napthyl salicylate, 2-napthyl salicylate, 2,4,6-tribromo-m-cresol, and 3',4', 5-trichlorosalicylanilide; lactones such as propiolactone; and ureas such as noxytiolin, polynoxylen, and triclocarbon.

Examples of other biocides suitable for use in the invention include chlorhexidine, chlorhexidine gluconate, chlorhexidine acetate, chlorhexidine hydrochloride, dibromopropamidine, halogenated diphenylalkanes, dibromsalan, metabromsalan, tribromsalan, carbanilide, salicylanilide, tetrachlorosalicylanilide, trichlorocarbanilide, propamidine isethionate, pentamidine, picloxydine, mendalamine, the acid addition and quaternary, methenamine mandelate, polyoxymethylene esters such as polyoxymethylene diester, polyoxymethylene diacetate and the like, and mixtures thereof.

Antiseptics that can be employed as the biocides used in the present invention include guanidines, such as alexidine and ambazone; halogens and halogen compounds, such as bornyl chloride, calcium iodate, cloflucarban, flurosalan, iodic acid, sodium hypochlorite, sodium iodate, symclosene, thymol iodide, triclocarban, triclosan and troclosene potassium; mercurial compounds, such as hydragaphen, meralein sodium, merbromin, ammoniated, mercuric sodium p-phenolsulfonate, mercuric succinimide, mercuric sulfide, red, mercurophen, mercurous acetate, mercurous chloride, mercurous iodide, nitromersol, thimerfonate sodium and thimerosal; and others, such as, aluminum acetate solution, aluminum subacetate solution, aluminum sulfate, 3-amino-4-hydroxybutyric acid, boric acid, chloroazodin, m-cresyl acetate, cupric sulfate, ichthammol, negatol, ornidazole, β-propiolactone, and α-terpineol.

Useful biocides also include paraformaldehyde polymer. The paraformaldehyde polymer used as a biocide is selected from the group consisting of the cyclic tripolymer of the general formula $(CH_2O)_n$ where n is 3 and the linear polymer of the general formula $HO(CH_2O)_mH$ wherein m is 3 to 125. These polymers are white crystalline solids, and in the presence of moisture undergo depolymerization to yield the water soluble biocide and disinfectant formaldehyde; see the *Encyclopedia of Chemical Technology*, Kirk-Othmer, Vol. 10, page 81, 1966, published by John Wiley & Sons, Inc., New York. In operation, the paraformaldehyde is moisture-activated by fluid from the surroundings causing it to depolymerize to formaldehyde. The formaldehyde acts as a biocide, or disinfectant to control the presence of microorganisms. Generally, in the presence of moisture, or in the presence of moisture and an acid catalyst, the cyclic and linear polymers are converted up to 99% formaldehyde, which is released over a prolonged period of time.

Especially preferred biocides include chlorhexidine gluconate, chlorhexidine acetate, chlorhexidine diacetate, triclosan, chloroxylenol, dequalinium chloride, benzethonium chloride, benzalkonium chloride and combinations thereof. In some embodiments, the one or more biocidal agents are present in an amount of about 0.01-10 wt. %, or about 0.01-5 wt. %, based on the total weight of the antimicrobial composition.

In addition to the alcohol and biocidal agent, the antimicrobial compositions of the present invention further comprise one or more poloxamers. Poloxamers are nonionic polyoxyethylene-polyoxypropylene block copolymers. Suitable poloxamers can comprise, for example, a hydrophobic segment of polyoxypropylene and hydrophilic segments of polyoxyethylene, such as those having a chemical formula:

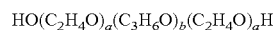

$$HO(C_2H_4O)_a(C_3H_6O)_b(C_2H_4O)_aH$$

where a is at least 12 and b is an integer such that the hydrophilic portion represented by $(C_2H_4O)$ constitutes about 50 to 90% by weight of the entire copolymer. Preferably, the average molecular weight is between about 2,000 to about 18,000 daltons. Non-limiting examples of suitable poloxamers include those presented in Table 1:

TABLE 1

| Poloxamer (USP grade) | a | b | Average Molecular Weight (daltons) |
|---|---|---|---|
| 124 | 12 | 20 | 2090 to 2360 |
| 188 | 80 | 27 | 7680 to 9510 |
| 237 | 64 | 37 | 6840 to 8830 |
| 338 | 141 | 44 | 12700 to 17400 |
| 407 | 101 | 56 | 9840 to 14600 |

In the USP designation, the non-proprietary name "poloxamer" is followed by a number, the first two digits of which, when multiplied by 100, correspond to the approximate average molecular weight of the polyoxypropylene portion of the copolymer, and the third digit, when multiplied by 10, corresponds to the percentage by weight of the polyoxyethylene portion.

Poloxamers are also known by other names such as methyl oxirane polymers, polymer with oxirane; polyethylene-polypropylene glycol polymers; and α-hydro-ω-hydroxypoly(oxyethylene)-poly(oxypropylene)poly(oxyethylene) block copolymers. Non-limiting examples of suitable poloxamers include PLURONIC® NF Grade block copolymers, such as PLURONIC® L44NF poloxamer 124, PLURONIC®F68NF poloxamer 188, PLURONIC® F87NF poloxamer 237, PLURONIC® F108NF poloxamer 338, and PLURONIC® F127NF poloxamer 407, which are commercially available from BASF Corporation of Mt. Olive, N.J. Preferred poloxamers are poloxamer 188, poloxamer 237 and poloxamer 407.

The one or more poloxamers are present in an amount of about 0.01 wt. % to 5 wt. %, or about 0.1 wt. % to 2 wt. %, based on the total weight of the antimicrobial composition.

While not wishing to be bound by any theory, it is thought that the use of a poloxamer surfactant in the locking composition may work in concert with the alcohol to allow the composition to penetrate into the catheter material itself. Further, the poloxamer may act to bind to the surface of the catheter. In this manner, it is thought that the poloxamer may act to prolong the release rate of the composition from the catheter surface, and/or may act to slow the leaching rate of the composition which has penetrated into the catheter material. In this manner, as the biocidal agent within the lumen of the catheter is depleted, the biocidal agent believed to be stored within the catheter material leaches out or is slowly released from the catheter material, thereby replenishing the biocidal agent and thus providing on-going and prolonged antimicrobial activity.

Poloxamers are compatible with blood and are non-toxic. Locking solutions commonly contain anticoagulants to remove coagulated blood from the catheter to prevent blockage. Poloxamers have anticoagulant activity, thus eliminating the need for an additional compound having this activity in the composition. Also, poloxamers can clean the inside of the catheter and eliminate the buildup of red blood cells or a biofilm which can lead to infection.

The antimicrobial composition optionally further comprises an additive. Suitable additives include, but are not limited to, anticoagulants, saline, water and combinations of these. When a salt is used in the formula, water may be necessary as a carrier for the salt, and can be present in an amount of about 5 wt. % to 45 wt. %, based on the total weight of the antimicrobial composition. Water or saline will typically make up the balance of the composition, after the other ingredients are added.

As used herein, the term "anticoagulant" is intended to mean any compound that has the ability, either directly or indirectly, to prevent the coagulation of blood or to dissolve blood clots or other coagulated species once formed. Examples of such compounds include, but are not limited to, di-ammonium hydrogen citrate, di-ammonium tartrate, citric acid, citric acid disodium salt, citric acid monopotassium salt, citric acid monosodium salt, citric acid tripotassium salt, citric acid trisodium salt, ethylenediaminetetraacetic acid (EDTA), EDTA diammonium salt, EDTA dipotassium salt, EDTA disodium salt, EDTA tetrasodium salt, ethylenebis(oxyethylenenitrilo)tetraacetic acid (EGTA), EDTA trisodium salt, EDTA tripotassium salt, ethylene glycol-O,O'-bis(2-aminoethyl)-N,N,N',N'-tetraacetic acid, N-(2-hydroxyethyl)ethylenediamine-N,N',N'-triacetic acid trisodium salt, nitrilotriacetic acid, potassium sodium tartrate, potassium hydrogen D-tartrate, L-tartaric acid dipotassium salt, L-tartaric acid disodium salt, L-tartaric acid monosodium salt, heparin, warfarin, acetylsalicylic acid, ibuprofen, indomethacin, prostaglandins, sulfinpyrazone, streptokinase, urokinase, tissue plasminogen activator (TPA), coumarin, protamine sulfate, anti-thrombin III, coumadin, protein C/protein S, nicoumalone, phenprocoumon, hirudin, hirulog, and the like. Mixtures of the foregoing can be employed. A preferred anticoagulant is EDTA. When present, the anticoagulant will be used in an amount of about 0.01-3 wt. %, more preferably between about 0.1-1 wt. %, based on the total weight of the antimicrobial composition.

The compositions of the present invention can be prepared with simple mixing at room temperature. Typically, alcohol and any water used will be mixed first, followed by the addition of the other ingredients, in any order.

In some embodiments, the present invention provides methods for providing long term disinfection of an implanted catheter comprising introducing the antimicrobial composition or an antimicrobial composition comprising the same, into a lumen of the catheter, the antimicrobial composition comprising at least one lower alcohol, at least one antimicrobial agent and at least one poloxamer. In other embodiments, the composition can comprise at least one lower alcohol and at least one poloxamer. Preferably, the lumen of the catheter is substantially filled with the antimicrobial composition. The composition is introduced into the catheter in the time periods between medical uses, such as for example between infusions of blood, pharmaceuticals, nutrients, and the like. The antimicrobial compositions of the present invention can provide biocidal activity for period of about 48 hours up to about one week.

In other embodiments, the present invention provides methods for disinfecting a catheter comprising coating at least a portion of an interior surface of the catheter, and optionally any exterior surfaces desired, with a coating of an antimicrobial composition comprising at least one lower alcohol, at least one antimicrobial agent and at least one poloxamer or an antimicrobial composition comprising at least one lower alcohol and at least one poloxamer as described in detail above.

Typically, the composition is used to lock catheters made of polyurethane or silicone materials, but other types of catheters, as well as other types of medical devices made of similar materials, can be used in combination with the composition.

EXAMPLES

The following examples are intended to illustrate the invention and should not be construed as limiting the invention in any way.

Formulations 1-14 were prepared with the ingredients described below in Table 2, with the amounts shown in Table 3:

TABLE 2

| Ingredient | Supplier |
|---|---|
| Ethanol (90 proof) | VWR International, Inc. West Chester, Pennsylvania |
| Isopropyl Alcohol - (IPA) (>99% alcohol) | JT Baker Phillipsburg, New Jersey |
| Chlorhexidine Gluconate (20%) | Xttrium Laboratories Chicago, Illinois |
| Saline | JT Baker Phillipsburg, New Jersey |
| Ethylenediamine-tetraacetic acid powder - (EDTA) USP water | The Dow Chemical Company Midland, Michigan |
| PLURONIC ® F 68 Poloxamer 188 | BASF Mt. Olive, New Jersey |

TABLE 3

| | Formula 1 | Formula 2 | Formula 3 | Formula 4 | Formula 5 | Formula 6 | Formula 7 | Formula 8 | Formula 9 | Formula 10 | Formula 11 | Formula 12 | Formula 13 | Formula 14 |
|---|---|---|---|---|---|---|---|---|---|---|---|---|---|---|
| Ethanol | 70 | 70 | 70 | 70 | 70 | 70 | 70 | 70 | 70 | 70 | 70 | — | — | — |
| IPA | — | — | — | — | — | — | — | — | — | — | — | 70 | 70 | 70 |
| Chlorhexidine Gluconate (20%) | 2.5 | 0.5 | 0.25 | 2.5 | 0.5 | 0.25 | 2.5 | 0.5 | 0.25 | 0.5 | 0.5 | 2.5 | 0.5 | 0.25 |
| Saline | 27.5 | 29.5 | 29.75 | — | — | — | — | — | — | 28.9 | — | — | 28.9 | 29.75 |
| EDTA | 0.0 | — | — | 0.1 | 0.1 | 0.1 | 0.1 | — | — | 0.1 | — | — | 0.1 | — |
| USP water | — | — | — | 27.4 | 29.4 | 29.65 | 27.0 | 29.0 | 29.25 | — | 29.0 | 27.4 | — | — |
| Poloxamer | 0.0 | — | — | — | — | — | 0.5 | 0.5 | 0.5 | 0.5 | 0.5 | — | 0.5 | — |

Zone Inhibition

Tubing samples which had been dipped in the compositions according to Formulations 1-10 were tested for their ability to inhibit growth of various microorganisms. In particular, two sets of tubing represented as Tubing A and B were provided.

Tubing A is Tecoflex® polyurethane tubing available from Noveon, Inc. of Cleveland, Ohio, and is a type of tubing typically used in central venous catheters. Tubing B is polyurethane tubing available from Becton Dickinson of Franklin Lakes, N.J., typically used in peripheral catheters. The tubing samples were not precleaned prior to testing. For each sample, approximately 5 mm of tubing material was dipped in the respective antimicrobial composition of Formulations 1-10 (at room temperature) and dried in an oven. A control sample of tubing that had not been dipped in any formulation was also tested. The tubing was then placed on agar plates coated with trypticase soy broth growth medium seeded with common microorganisms of Pseudomonas aeruginosa, Candida albicans, Escherichia coli or Staphylococcus aureus. One ml of $10^8$-$10^9$ of the test organism was spread over each agar plate and incubated at 30°-35° C. The plates were examined at 24 hours, 48 hours and 72 hours and the radius of the area (mm) in which growth of the microorganisms was inhibited was measured by visual inspection. The results are shown in Tables 4-7.

TABLE 4

Zones of Inhibition in Millimeters of Samples of Tubing Challenged with P. aeruginosa

|  | Tubing A | Tubing B |
|---|---|---|
| Control | 0 | 0 |
| Formulation 1 | 0 | 0 |
| Formulation 2 | 0 | 0 |
| Formulation 3 | 0 | 0 |
| Formulation 4 | 0 | 0 |
| Formulation 5 | 0 | 0 |
| Formulation 6 | 0 | 1 |
| Formulation 7 | 3 | 3 |
| Formulation 8 | 0 | 0 |
| Formulation 9 | 0 | 0 |
| Formulation 10 | 0 | 0 |

TABLE 5

Zones of Inhibition in Millimeters of Samples of Tubing Challenged with C. albicans

|  | Tubing A | Tubing B |
|---|---|---|
| Control | 0 | 0 |
| Formulation 1 | 0 | 0 |
| Formulation 2 | 0 | 1 |
| Formulation 3 | 0 | 0 |
| Formulation 4 | 2 | 3 |
| Formulation 5 | 1 | 0 |
| Formulation 6 | 1 | 0 |
| Formulation 7 | 3 | 3 |
| Formulation 8 | 0 | 1 |
| Formulation 9 | 0 | 0 |
| Formulation 10 | 0 | 0 |

TABLE 6

Zones of Inhibition in Millimeters of Samples of Tubing Challenged with E. coli

|  | Tubing A | Tubing B |
|---|---|---|
| Control | 0 | 0 |
| Formulation 1 | 2 | 1 |
| Formulation 2 | 0 | 1 |
| Formulation 3 | 0 | 1 |
| Formulation 4 | 2 | 2 |
| Formulation 5 | 1 | 1 |
| Formulation 6 | 1 | 1 |
| Formulation 7 | 2 | 4 |
| Formulation 8 | 2 | 1 |
| Formulation 9 | 0 | 0 |
| Formulation 10 | 1 | 1 |

TABLE 7

Zones of Inhibition in Millimeters of Samples of Tubing Challenges with S. aureus

|  | Tubing A | Tubing B |
|---|---|---|
| Control | 0 | 0 |
| Formulation 1 | 3 | 2 |
| Formulation 2 | 3 | 3 |
| Formulation 3 | 1 | 1 |
| Formulation 4 | 4 | 3 |
| Formulation 5 | 2 | 1 |
| Formulation 6 | 2 | 2 |
| Formulation 7 | 5 | 5 |
| Formulation 8 | 3 | 2 |
| Formulation 9 | 0 | 0 |
| Formulation 10 | 2 | 2 |

As shown in Table 4, for example, the tubing dipped in Formulation 7 according to the invention prevented growth of P. aeruginosa microorganisms within a 3 mm zone surrounding the tubing, for both tubing A and B samples. Formulations 8-10, having lower amounts of chlorhexidine gluconate, inhibited growth, but did not perform as well as Formulation 7. Across all tested organisms (Tables 4-7), the formulation having the highest amount of chlorhexidine gluconate (Formulation 7) performed the best in terms of inhibiting growth of the tested microorganisms. While not intending to be bound by any theory, it is believed that polaxamer can bind to the catheter material and prolong the release rate of the antimicrobial composition.

Bactericidal Effectiveness Test

Formulations 1 through 10 were evaluated for biocidal effectiveness against target microorganisms, namely S. aureus, P. Aeruginosa, C. Albicans and E. Coli. These are standard microorganisms representing gram positive, gram negative and fungus classifications. The biocidal effectiveness testing procedure was conducted as follows:

Five milliliters of each formulation was added to a sterile tube. A microbial challenge of 0.1 ml containing the target microorganisms with appropriate count (one ml containing about $10^8$-$10^9$ organisms) was added to the 5 ml test solution. At exposure times of 1 minute and 5 minutes, a 1.0 ml sample was transferred to 9.0 ml of Difco Dey Engley neutralizing broth. Subsequent 1.0 ml samples were transferred to Difco Dey Engley neutralizing broth base. All samples were incubated at 30 to 33° C. for 48 hours.

The results of the effectiveness testing of the formulations are shown in Table 8. All bacteria tested were killed after contact with these solutions for one minute.

TABLE 8

Germicidal Efficacy Testing
(Results for all 10 Formulations at Full Strength)

| Formulation Number | Time Increment | E. coli | P. aeruginosa | S. aureus | C. albicans |
|---|---|---|---|---|---|
| 1 | 1 minute | – | – | – | – |
| 1 | 5 minutes | – | – | – | – |
| 2 | 1 minute | – | – | – | – |
| 2 | 5 minutes | – | – | – | – |
| 3 | 1 minute | – | – | – | – |
| 3 | 5 minutes | – | – | – | – |
| 4 | 1 minute | – | – | – | – |
| 4 | 5 minutes | – | – | – | – |
| 5 | 1 minute | – | – | – | – |
| 5 | 5 minutes | – | – | – | – |
| 6 | 1 minute | – | – | – | – |
| 6 | 5 minutes | – | – | – | – |
| 7 | 1 minute | – | – | – | – |
| 7 | 5 minutes | – | – | – | – |
| 8 | 1 minute | – | – | – | – |
| 8 | 5 minutes | – | – | – | – |
| 9 | 1 minute | – | – | – | – |
| 9 | 5 minutes | – | – | – | – |
| 10 | 1 minute | – | – | – | – |
| 10 | 5 minutes | – | – | – | – |

(–) = no growth
(+) = growth
No growth indicates effective antimicrobial activity
Growth indicates lack of effective antimicrobial activity Whereas particular embodiments of this invention have been described above for purposes of illustration, it will be evident to those skilled in the art that numerous variations of the details of the present invention may be made without departing from the invention as defined in the appended claims.

What is claimed is:

1. A catheter containing a locking solution comprising an antimicrobial composition, the antimicrobial composition comprising:
   at least one poloxamer;
   at least 10 weight percent of at least one alcohol on a basis of total weight of the antimicrobial composition; and
   about 0.01 wt. % to about 10 wt. % on the basis of total weight of the antimicrobial composition of at least one biocidal agent that is not an alcohol.

2. The catheter of claim 1, wherein the poloxamer is represented by the formula

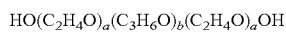

where a is at least 12 and b is an integer such that the hydrophilic portion represented by ($C_2H_4O$) constitutes about 50 to about 90% by weight of the entire polymer.

3. The catheter of claim 2, wherein the average molecular weight of the poloxamer is between about 2,000 to about 18,000 daltons.

4. The catheter of claim 3, wherein the at least one poloxamer is selected from the group consisting of poloxamer 188, poloxamer 237 and poloxamer 407.

5. The catheter of claim 1, wherein the poloxamer is present in an amount of about 0.01 wt. % to about 5 wt. %, based on the weight of the antimicrobial composition.

6. The catheter of claim 1, wherein the at least one biocidal agent that is not an alcohol is selected from the group consisting of β-propiolactone, α-terpineol, 1-(3-choroallyl)-3,5,7-triazo-1-azoniaadamantane chloride, 1,4-dihydro-1-ethyl-6-fluoro-4-oxo-7-(1-piperazinyl)-3-quinolinecarboxylic acid, 1-cyclopropyl-6-fluoro-1,4-dihydro-4-oxo-7-(1-piperazinyl)-3-quinolinecarboxylic acid, 1-napthyl salicylate, 2-(methoxymethyl)-5-nitrofuran, 2,4,4'-trichloro-2'-hydroxydiphenol, 2,4,6-tribromo-m-cresol, 2-bromo-2-nitropropan-1,3-diol, 2-napthyl salicylate, 3,4,4'-trichlorocarbanilide, 3,4',5-tribromosalicylanilide, 3',4',5-trichlorosalicylanilide, 3-amino-4-hydroxybutyric acid, 3-trifluoromethyl-4,4'-dichlorocarbanilide, 5-nitro-2-furaldehyde semicarbazone, 8-hydroxyquinoline sulfate, 8-hydroxyquinoline, acetic acid, acetomeroctol, acridine, acriflavine, alexidine, aluminum acetate solution, aluminum subacetate solution, aluminum sulfate, ambazone, amide, amidine, aminacrine hydrochloride, aminoquinuride, ammoniated, mercuric sodium p-phenolsulfonate, amylmetacresol, benzalkonium chloride, benzethonium chloride, benzoic acid, benzoxiquine, bisphenols, bithionol, boric acid, bornyl chloride, bromochlorobisphenol, broxyquinoline, calcium hypochlorite, calcium iodate, carbamates, carbanilide, carbanilide, carvacol, cetrimide, cetylpyridinium chloride, chelate and imidazoline biocides, chloramine, chlorasine, chlorhexidine acetate, chlorhexidine gluconate, chlorhexidine hydrochloride, chlorhexidine, chlorinated phenol, chlorine-releasing biocides, chloroazodin, chlorocresol, chlorophene, chlorothymol, chloroxine, chloroxylenol, chlorphenoctium amsonate, chlorquinaldol, cloflucarban, cloxyquin, cresol, crystal violet, cupric sulfate, dehydroacetic acid, dequalinium acetate, dequalinium chloride, dequalinium, dibromopropamidine, dibromsalan, dichloramine, dichlorobisphenol, dichlorodimethylhydantoin, dichloroglycoluril, dichloroisocyanurate, dichloroxylenol, domiphen bromide, ethylenediaminetetraacetic acid, esters of p-hydroxybenzoic acid, ethylhydrocupreine, euprocin, fenticlor, flurosalan, formaldehyde, furaltadone, furazolidone, glutaraldehyde, griseofulvin, guanide, halane, halazone, halogenated dialkyl-hydantoin, halogenated diphenylalkanes, halquinol, hexachlorophene, hexamethylenetetramine, hydragaphen, hydrastine, hydrogen peroxide, hydroxyquinoline, ichthammol, iodic acid, iodine, iodochlorhydroxyquin, lactone, laurolinium acetate, laurolinium, lioquinol, magenta, m-cresyl acetate, mendalamine, meralein sodium, merbromin, mercuric succinimide, mercuric sulfide, mercurophen, mercurous acetate, mercurous chloride, mercurous iodide, metabromsalan, methenamine mandelate, methylbenzethonium chloride, myristyl-gamma-picolinium chloride, N(5-nitro-2-furfurylidene)-1-amino-hydantoin, negatol, nidroxyzone, nifuroxime, nifurzide, nitrofurantoin, nitrofurazone, nitrofurfural, nitromersol, noxythiolin, noxytiolin, ornidazole, ortaphonium chloride, oxychlorosene, parachlorometaxylenol, paraformaldehyde polymer, pararosaniline, p-chlorophenol, pentamidine, peracetic acid, phenol, picloxydine, polynoxylen, polyoxymethylene diacetate, polyoxymethylene diester, potassium hypochlorite, povidone-iodine, p-phenylphenol, proflavin hemisulfate, propamidine isethionate, propiolactone, propionic acid, pyridinium biocides, quaternary ammonium biocides, quinaldinium, quinoline, quinone, red, rosaniline, salicylamide, salicylanilide, scarlet red, silver nitrate, silver sulfadiazine, sodium hypochlorite, sodium iodate, sodium oxychlorosene, sorbic acid, succinchlorimide, sulfa, sulfurous acid, symclosene, taurolidine, taurultam, tetrachlorosalicylanilide, thimerfonate sodium, thimerosal, thiosemicarbazone, thymol iodide, thymol, tribromsalan, trichlorocarbanilide, trichloroisocyanuric acid, trichloromelamine, triclobisonium chloride, triclocarban, triclocarbon, triclosan and troclosene potassium, trinitrophenol, triphenylmethane, and vanillic acid.

7. The catheter of claim 1, wherein the at least one biocidal agent that is not an alcohol is selected from the group consisting of benzalkonium chloride, benzethonium chloride, chlorhexidine diacetate, chlorhexidine gluconate, chloroxylenol, dequalinium chloride, triclosan, and combinations thereof.

8. The catheter of claim 7, wherein the at least one biocidal agent that is not an alcohol is chlorhexidine gluconate.

9. The catheter of claim 1, wherein the alcohol is a $C_1$-$C_6$ lower alcohol.

10. The catheter of claim 9, wherein the $C_1$-$C_6$ lower alcohol is a mixture of isopropyl alcohol and ethanol.

11. The catheter of claim 10, wherein the at least one lower alcohol is a mixture of isopropyl alcohol and ethanol and is present in an amount of about 50 to about 95% by weight of the antimicrobial composition.

12. The catheter of claim 1, further comprising an additive selected from the group consisting of an anticoagulant, saline, water and combinations thereof.

13. The catheter of claim 12, wherein the anticoagulant is selected from the group consisting of acetylsalicylic acid, anti-thrombin III, citric acid disodium salt, citric acid monopotassium salt, citric acid monosodium salt, citric acid tripotassium salt, citric acid trisodium salt, citric acid, coumadin, coumarin, di-ammonium hydrogen citrate, di-ammonium tartrate, ethylenediaminetetraacetic acid (EDTA) diammonium salt, EDTA dipotassium salt, EDTA disodium salt, EDTA tetrasodium salt, EDTA tripotassium salt, EDTA trisodium salt, ethylene glycol-O,O'-bis(2-aminoethyl)-N,N,N',N'-tetraacetic acid, ethylenebis(oxyethylenenitrilo)tetraacetic acid, EDTA, heparin, hirudin, hirulog, ibuprofen, indomethacin, L-tartaric acid dipotassium salt, L-tartaric acid disodium salt, L-tartaric acid monosodium salt, N-(2-hydroxyethyl)ethylenediamine-N,N',N'-triacetic acid trisodium salt, nicoumalone, nitrilotriacetic acid, phenprocoumon, potassium hydrogen D-tartrate, potassium sodium tartrate, prostaglandins, protamine sulfate, protein C/protein S, streptokinase, sulfinpyrazone, tissue plasminogen activator (TPA), urokinase and warfarin.

14. The catheter of claim 12, wherein the anticoagulant is ethylenediaminetetraacetic acid.

15. The catheter of claim 1, wherein at least one interior surface of the catheter is coated with the antimicrobial composition.

16. A catheter comprising a coating comprising an antimicrobial composition, the antimicrobial composition comprising:

0.1 weight percent on a basis of total weight of the antimicrobial composition to 2 weight percent of at least one poloxamer;

at least 10 weight percent of at least one $C_1$-$C_6$ lower alcohol on a basis of total weight of the antimicrobial composition;

about 0.01 wt. % to about 10 wt. % on the basis of total weight of the antimicrobial composition of at least one biocidal agent that is not an alcohol; and an anticoagulant.

17. A method for providing disinfection of an implanted catheter comprising a lumen and a wall, the method comprising:

introducing a locking solution comprising an antimicrobial composition into the lumen of the catheter, the antimicrobial composition comprising:

at least one poloxamer;

at least 10 weight percent of at least one alcohol on a basis of total weight of the antimicrobial composition; and about 0.01 wt. % to about 10 wt. % on the basis of total weight of the antimicrobial composition of at least one biocidal agent that is not an alcohol.

18. The method of claim 17, wherein the at least one poloxamer is present in an amount of about 0.01 wt. % to 5 wt. %, based on the total weight of the antimicrobial composition.

19. The method of claim 17, wherein the alcohol is a $C_1$-$C_6$ lower alcohol.

20. The method of claim 19, wherein the $C_1$-$C_6$ lower alcohol is a mixture of isopropyl alcohol and ethanol.

21. The method of claim 19, wherein the at least one lower alcohol is a combination of isopropyl alcohol and ethanol to a total in the range of 50 to 95 wt %, based on the weight of the antimicrobial composition.

22. The method of claim 17, wherein the antimicrobial composition is maintained in the lumen of the catheter for a period of time ranging from about 48 hours to about one week.

23. The method of claim 17, wherein the antimicrobial composition penetrates the wall of the catheter.

* * * * *

UNITED STATES PATENT AND TRADEMARK OFFICE
CERTIFICATE OF CORRECTION

PATENT NO. : 9,872,941 B2
APPLICATION NO. : 15/486893
DATED : January 23, 2018
INVENTOR(S) : Minh Quang Hoang It is certified that error appears in the above-identified patent and that said Letters Patent is hereby corrected as shown below:

Column 13, Line 64, Claim 6, delete "choroallyl)" and insert -- chloroallyl) --

Column 13, Line 67, Claim 6, delete "1-napthyl" and insert -- 1-naphthyl --

Column 14, Line 3, Claim 6, delete "2-napthyl" and insert -- 2-naphthyl --

Column 14, Lines 16-17, Claim 6, delete "carbanilide, carbanilide," and insert -- carbanilide, --

Column 14, Line 17, Claim 6, delete "carvacol," and insert -- carvacrol, --

Column 14, Line 31, Claim 6, delete "flurosalan," and insert -- fluorosalan, --

Column 14, Lines 37-38, Claim 6, delete "lioquinol," and insert -- clioquinol, --

Column 14, Line 38, Claim 6, delete "mendalamine," and insert -- mandelamine, --

Column 14, Line 49, Claim 6, delete "polynoxylen," and insert -- polynoxylin, --

Column 16, Line 36, Claim 21, delete "wt %," and insert -- wt. %, --

Signed and Sealed this
Twenty-ninth Day of May, 2018

Andrei Iancu
*Director of the United States Patent and Trademark Office*